US006906027B2

(12) United States Patent
Oki et al.

(10) Patent No.: US 6,906,027 B2
(45) Date of Patent: Jun. 14, 2005

(54) COMPOSITION FOR NASAL ADMINISTRATION OF INSULIN

(75) Inventors: Toshikazu Oki, Yokohama (JP); Takashi Hanafusa, Kobe (JP); Shunji Haruta, Kagoshima (JP)

(73) Assignee: Translational Research Ltd., Kagoshima (JP)

( * ) Notice: Subject to any disclaimer, the term of this patent is extended or adjusted under 35 U.S.C. 154(b) by 0 days.

(21) Appl. No.: 10/250,862

(22) PCT Filed: Jul. 3, 2002

(86) PCT No.: PCT/JP02/06721

§ 371 (c)(1), (2), (4) Date: Jul. 9, 2003

(87) PCT Pub. No.: WO03/004048

PCT Pub. Date: Jan. 16, 2003

(65) Prior Publication Data

US 2004/0063615 A1 Apr. 1, 2004

(30) Foreign Application Priority Data

Jul. 5, 2001 (JP) .................................... 2001-204784

(51) Int. Cl.[7] .............................................. A61K 38/28
(52) U.S. Cl. .......................................... 514/3; 530/303
(58) Field of Search ......................... 514/3, 4; 530/303, 530/304

(56) References Cited

FOREIGN PATENT DOCUMENTS

| | | |
|---|---|---|
| EP | 122036 | 11/1994 |
| EP | 0 943 326 | 9/1999 |
| JP | 60-224616 | 11/1985 |
| JP | 62-42888 | 9/1987 |
| JP | 63-115821 | 5/1988 |
| JP | 08-277226 | 10/1996 |
| JP | 10-59841 | 3/1998 |

*Primary Examiner*—Jeffrey Edwin Russel
(74) *Attorney, Agent, or Firm*—Wenderoth, Lind & Ponack, L.L.P.

(57) ABSTRACT

Provided is an insulin-containing granulated composition for nasal administration comprising a crystalline cellulose aggregate having a specific particle diameter distribution as a carrier. Such granulated composition for nasal administration can efficiently increase a blood insulin concentration.

11 Claims, 4 Drawing Sheets

Insulin concentration (μU/mL)
500
450
400
350
300
250
200
150
100
50
0
0 1 2 3 4
Time after administration (hour)

COMPOSITION FOR NASAL ADMINISTRATION OF INSULIN

TECHNICAL FIELD

The present invention relates to a pharmaceutical formulation, the distinguishing features of which are that it is granular in form and is administered via the nasal mucosa. Specifically, the present invention relates to a granulated composition of insulin for nasal administration as a therapeutic treatment for diabetes.

BACKGROUND ART

At present, the insulin used in the clinical treatment of diabetes is in the form of an injectable formulation, and in most cases is self-administered by a comparatively simple subcutaneous injection. The characteristics of this type of drug are such that the patient must self-administer before meals, once to four times a day for life. This troublesome procedure is only one of the many problems associated with the treatment of diabetes.

Preparations for nasal administration have been proposed as a remedy to the difficulties associated with subcutaneous administration. For example, an insulin formulation in which 90 w/w % of the particle diameters ranged from 20–150 μm, using crystalline cellulose as a basic material was described in JP-6242888-B. Under the suggestion that 'Physiological polypeptides for nasal mucosal absorption are preferably water-soluble' in this preparation, the practical example described in the said publication show a formulation in which 90 w/w % or more of the particle diameters ranged from 75–149 μm can be obtained after dissolving insulin in 0.1N HCl, freeze-drying, mining the soluble insulin thus obtained with crystalline cellulose, and sifting.

In comparison with the above-mentioned JP-6242888-B, JP-1059841-A (corresponding to EP-943326-A1) with regard to high hydrophilic drugs, high lipophilic drugs and peptides with high molecular weight, describes an excellent example of compositions with superior nasal absorption and increased maximum blood concentrations. According to this official gazette, this action effect can be positively achieved using a water-absorbing and basic gel-forming base such as hydroxypropylcellulose in combination with aggregate crystalline cellulose of particle diameter greater than 150 μm on the contrary to JP-6242888-B suggesting that a relatively small particle diameter of 20–150 μm is preferred as the preparation.

However, the present inventors have no information on the practical application of insulin formulations for nasal administration including these related prior arts. A composition that will enable nasal administration of insulin for practical use and particularly markedly increased nasal insulin absorption, is, therefore, still needed.

DISCLOSURE OF THE INVENTION

The present inventors have found a nasal composition that unlike those described in the foregoing JP-6242888-B and JP-1059841-A uses non-solubilized powdered insulin and a special, aggregate crystalline cellulose with a particle diameter of less than 150 μm, which in comparison with existing compositions, significantly increases insulin absorption enabling enhanced therapeutic efficacy in the treatment of diabetes patients.

The present invention is based on this knowledge.

Accordingly, the present invention relates to powdered insulin composition for nasal administration that composed of powdered insulin and its carrier, aggregated crystalline cellulose, the distinguishing features of which are that the said insulin is non-solubilized, and 90 w/w % or more of said crystalline cellulose aggregate has a cribriform particle diameter range of 10–350 μm in one part or across the whole particle area.

Moreover, the present invention relates to powdered insulin composition for nasal administration that composed of powdered insulin and its carrier, aggregated crystalline cellulose, the distinguishing features of which are that the said insulin is not only non-solubilized but solubilized, and 85 w/w % or more of said crystalline cellulose aggregate has a cribriform particle diameter range of 20–60 μm in one part or across the whole area.

Another mode of the present invention relates to use of a crystalline cellulose aggregate as a carrier for preparing a granulated composition for nasal absorption, containing insulin, for the treatment of diabetes (in which 90 w/w % or more of the particles in the said aggregated crystalline cellulose has a cribriform particle diameter range of 10–350 μm in one part or across the whole area).

A further mode of the present invention relates to a therapeutic method for diabetes, spraying a granulated composition composed of powdered insulin and its carrier, aggregated crystalline cellulose (the distinguishing features of which are that the said insulin is non-solubilized, and 90 w/w % or more of said crystalline cellulose aggregate has a cribriform particle diameter range of 10–350 μm in one part or across the whole area) into the nasal cavity of diabetic patients at sufficient insulin doses for an effective diabetic treatment.

BEST MODE FOR CARRYING OUT THE INVENTION

Figure 1:
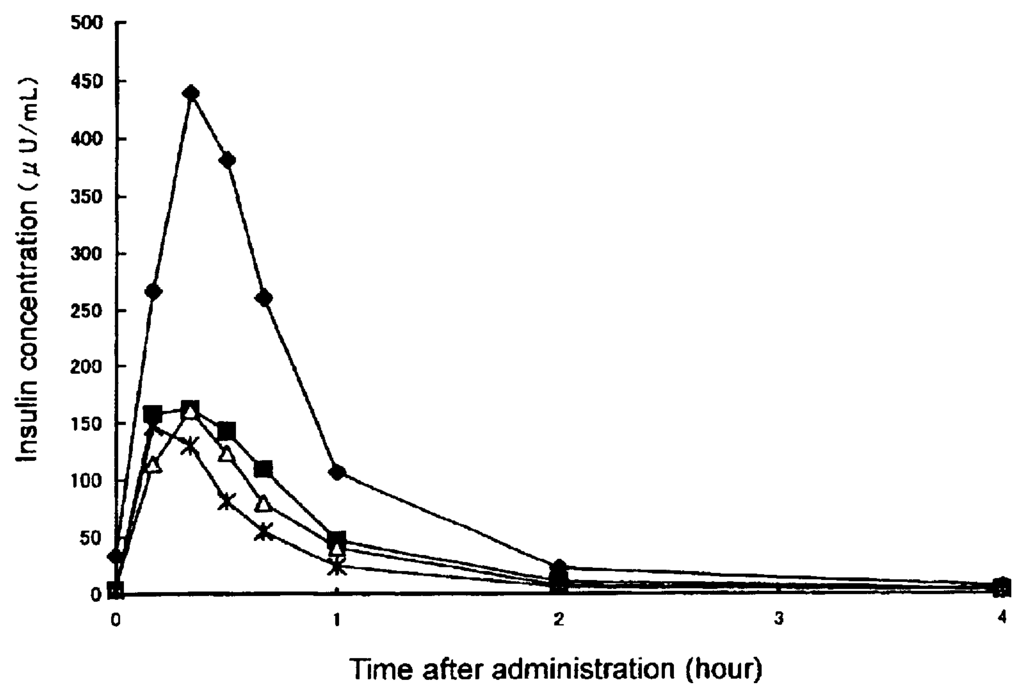
FIG. 1 is a graph showing changes in serum insulin concentrations after intranasal administration of each preparation in cynomolgus monkeys. -♦-, a preparation with Avicel® PH-F20; -■-, a preparation with Avicel® PH-F20 (solubilized insulin); -Δ-, a preparation with Avicel® PH-101; -*-, a preparation with Avicel® PH-101 (solubilized insulin).
Figure 2:
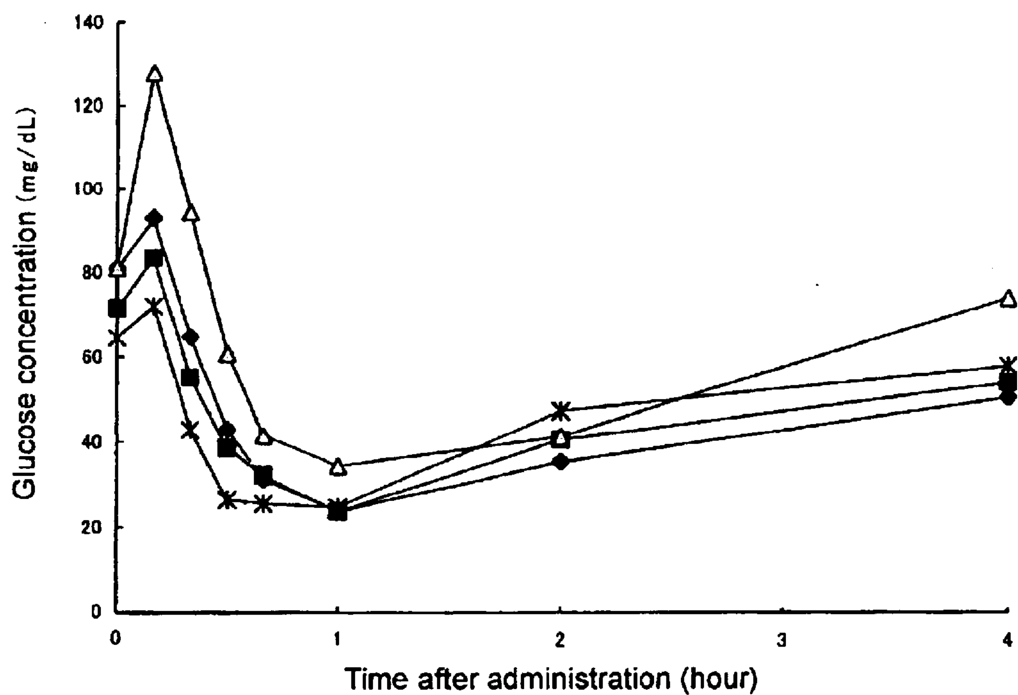
FIG. 2 is a graph showing changes in serum glucose concentrations after intranasal administration of each preparation in cynomolgus monkeys. The legends correspond to those in FIG. 1.

Any form of modified or unmodified insulin used in treating diabetes in humans can be used with the present invention, regardless of its origin. Accordingly, the term 'Insulin' as used here is deemed to mean all types in current or future clinical use, having the same physiologically activity as that of human insulin including human insulin, refined bovine insulin, refined porcine insulin, semi-synthesized human insulin, human isoinsulin, genetically modified human insulin or its variants thereof. Powder forms of these types of insulin or insulin that is only slightly soluble in water or almost insoluble in water (Corresponding to 1 g of powdered insulin requiring solvent in excess of 1000 mL and less than 10000 mL, or in excess of 10000 mL; see 13$^{th}$ Japan Pharmacopoeia, Principles of Operation A-51) even if modified, can also be preferably used with the present invention.

Given that the type of insulin described previously is slightly soluble in water or almost insoluble in water, insulin used with the present invention can be described as 'non-solubilized' powdered insulin. With regard to this, solubilized powdered insulin, including insulin other than the described above 'non-solubilized' powdered insulin, is typically understood to be a substance that has itself become solubilized by means of the known method of treatment described in JP-6242888-B. In general terms, solubilized insulin can be obtained by freeze-drying after producing an acidified aqueous insulin solution by means of a specific surfactant.

Insulin powder as described above can be of a finely powdered crystalline or non-crystalline structure, finer in comparison with the particulate cellulose described later, which composes aggregated crystalline cellulose. Generally, these multiple powders adhere to the surface of particulate cellulose or to the surface of microstructures (E.g. pores), or can also be of an encapsulating size. Generally, the various forms of insulin marketed in the form of medicinal powder can be used without alteration.

Generally, 'aggregated crystalline cellulose' as used in the present invention is refined from the water-insoluble part of a-cellulose that is obtained as a pulp from plant fiber and partially de-polymerized with acid. It is possible to use aggregated crystalline cellulose obtained from rayon fiber etc. provided that it meets the purpose of the present invention. Moreover, the size of that derived from Avicel®, or a variant thereof, as described in JP-3912469-B, JP-5638128-B, JP-6121201-B, and JP-0538732-B, can if necessary, be reduced by processing with a high-speed impact or air flow-type pulverizer, and/or the bulk density increased by fine pulverization, after which aggregated crystalline cellulose of required particle aggregate size can be obtained by classification or sifting for use with the present invention.

This kind of aggregated crystalline cellulose can usually be produced by de-polymerization as described above and there is no limit to its mean degree of polymerization provided that it meets the purpose of the present invention. Generally, however, crystalline cellulose having a mean polymerization degree between 15 and 400, more preferably 20 and 250, or ideally 30 and 50 can be selected. Although there is no restriction on the aggregated crystalline cellulose that can be utilized, that with a bulk density of 0.20–0.65 g/cm$^3$ is preferable and, 0.22–0.40 g/cm$^3$ is ideal. These bulk density values accord to measurement by the Scott Volumeter.

The principal factors demanded for aggregated crystalline cellulose that can be used with the present invention are the size and distributive pattern of the crystalline cellulose particles that constitute the aggregate. When expressed as the cribriform particle diameter range, particles should occupy a range of 10–350 $\mu$m partially, or 90 w/w % and above in their entirety.

Subsequent reference to particle size in this statement shall be taken to mean 'cribriform particle diameter', obtained from repeated sifting with standard screens, equal to the arithmetic or geometric mean of such screens unless otherwise stated.

This kind of aggregate, particularly in combination with non-solubilized insulin powder can be used. 'A part or whole area' can, be defined as, conforming to the particle size distribution as shown; for example, in Avicel® PH-101 or PH-301, in which 90 w/w % or more of the particles are distributed, for example, over a range of 10–150 $\mu$m as part of a diameter of 10–350 $\mu$m, or in which 90 w/w % or more of the particles are distributed over a whole area of 10–350 $\mu$m. These ranges, extending over a whole area of 10–150 $\mu$m, or a part thereof are acceptable if they comply to the present invention. Crystalline cellulose such as this can be obtained from the FMC Corporation of the United States and the Asahi Chemical Industrial Co., Ltd. as Avicel® PH-101, PH-301, and PH-M15 and may be used in the base form or obtained by grading.

A particle range extending over a whole area of 20–60 $\mu$m, or part thereof for example, aggregated crystalline cellulose in which approximately 85 w/w % or more of the particles are distributed over 20–approximately 40 $\mu$m, 20–approximately 55 $\mu$m, approximately 25–approximately 38 $\mu$m, approximately 25–approximately 53 $\mu$m or approximately 38–approximately 53 $\mu$m is more preferable. Specifically, Avicel® PH-F20 or PH-M15 can be graded or used as commercially available. While crystalline cellulose aggregate having a particle diameter is used jointly with water absorbent and gel-forming base materials in JP-1059841-A (or, EP-943326-A1), the use crystalline cellulose having particle diameters of 38–250 $\mu$m is shown as preferred mode, and the use of crystalline cellulose having a particle diameter of 100–250 $\mu$m is shown as the practical example. In the present invention, when using aggregated crystalline cellulose within more preferable particle diameter ranges as the described above, even when used only crystalline cellulose as carriers, a remarkable feature is the ability to achieve significantly higher insulin absorption after nasal administration of solubilized or non-solubilized insulin in comparison with the prior arts (even if it is not used jointly with water absorbent and gel-forming base materials in JP-1059841-A.).

Particularly preferred more specific crystalline cellulose, which can achieve such actions and effects include, includes but not limited to one having a particle distribution of:

10 w/w % or less of particle diameters below 25 $\mu$m,
20–60 w/w % of particle diameters of 25–38 $\mu$m,
20–60 w/w % of particle diameters greater than 38 $\mu$m and up to 53 $\mu$m, and 10 w/w % or less of particle diameters exceeding 53 μm, taking the entire particle as 100%.

Particularly favored are such aggregated crystalline cellulose that substantially do not contain particle diameters below 10 μm. The term 'substantially do not contain' as used in the present specification or invention shall be taken to mean no particle or present only a small percentage.

When according to the present invention, the mixing ratio of powdered insulin and the aggregated crystalline cellulose is adjusted to 1:1–500 w/w, and more preferably 1:2–100.

Composition that accord to the present invention can be prepared by homogenizing the above-mentioned powdered insulin and aggregated crystalline cellulose by a standard (for example, a blender, a mixer). The ambient conditions can be controlled, relative humidity should not exceed 60% and ideally should be below 40% at room temperature. Subsequently, if required, particles of less than 10 μm may be removed; however, the inventor needed no removal operations on the basis of their experience.

Compositions in a different form that accord to the present invention are, in addition to the above-mentioned compositions, acceptable provided that they do not exert any effect contrary to the purpose of the present invention, and this includes other carriers or base materials, excipients, preservatives, antiseptics, and absorption accelerants. For example, other carriers might include cellulose conductors such as hydroxypropylcellulose, hydroxypropylmethylcellulose, or methylcellulose as described in JP-1059841-A. When other carrier or diluting agents, are used in this manner, it is desirable that the compositions obtained be cribrated.

According to the method of preparation of the present invention, when the proportions of powdered insulin and aggregated crystalline cellulose used, particularly the insulin proportion, are not particularly high (e.g. 1/50 and above) or when excipients as mentioned above are not used, the particle diameter or particle distribution of the granulated composition obtained is substantially the same as that of the aggregated crystalline cellulose used. However if the particle diameter of the granulated composition significantly exceeds that of the aggregated crystalline cellulose, it is desirable that the composition be sifted to obtain the specified particle diameter. The term 'substantially the same' as used in this specification shall be taken to mean a maximum difference in comparison with the control diameter of 10% and ideally, no greater than 5%.

The composition of the nasally administered insulin thus obtained for the present invention can, when compared to conventional compositions, achieve remarkably high insulin absorption.

Accordingly, the granulated composition of the present invention enables the treatment of diabetes by nasal administration to patients. Nasal administration of such granulated composition is possible using any device capable of efficient delivery via the nasal mucosa, and devices already on the market (e.g.Jetlizer, Unisia Jecs Corporation.) may be used as they are.

The maximum or most appropriate dose to be administered to diabetes patients will vary according to individual cases and the severity of the condition, and can not therefore be readily prescribed. However, a medical specialist can, in consideration of serum insulin and glucose concentrations and efficacy following normal subcutaneous injection, determine the appropriate dosage in reference to the results of administration to both cynomolgus monkeys and healthy adult humans shown below.

Accordingly, the present invention also relates to a therapeutic method for diabetes using the granulated insulin composition mentioned above.

The present invention shall further be explained details of nasal delivery of granulated insulin according to the present invention and specific comparative examples, but it is not intended that the present invention be restricted to these. The insulin used in these examples was recombinant human insulin supplied by Intergene Co., Ltd.

Pharmacokinetic and Pharmacological Studies in Cynomolgus Monkeys

Unless specified, six male monkeys (body weight: 3–7 kg) in each study group were nasally administered once and serum insulin and glucose concentrations were measured chronologically.

Insulin and glucose concentrations were measured by Enzyme Immune Assay (EIA) and Glck•G•6•PDH, respectively.

Each pharmaceutical preparation was placed in a capsule, and administered intranasally with an administration device (Jetlizer, Unisia Jecs Corporation).

(1) 35 mg of powdered water-insoluble insulin (28.7 IU/mg), received as described above, and crystalline cellulose compositions [Asahi Chemical Industrial Co., Ltd.: Avicel® PH-101 and Avicel® PH-F20 (965 mg of each)], were thoroughly mixed in a mortar to prepare nasal administration compositions. 100 mg of powdered water-insoluble insulin was then dissolved in 1 mL of 0.1 N-hydrochloric acid, and water-soluble insulin was prepared by adding 40 mL of purified water to the insulin solution and freeze-drying. 36 mg of powdered, water-soluble insulin (27.7 IU/mg) obtained by this procedure and 964 mg of the above-mentioned crystalline cellulose were thoroughly mixed, and the composition for nasal administration was administered to cynomolgus monkeys (n=6). Pharmacokinetic parameters calculated from serum insulin concentrations after administration are shown in Table 1 (mean value±SD).

Serum insulin concentration and glucose concentration-time curves of each nasal absorption formulation stated above are shown in Tables 1 and 2, respectively. Raw data regarding Table 1 are shown in Tables 2 to 5.

TABLE 1

| | Kind of preparation | Dosage (IU/body) | Number of animals | $C_{max}$ (μU/mL) | $T_{max}$ (h) | $T_{1/2}$ (h) | $AUC_{0-4}$ (μU · h/mL) |
|---|---|---|---|---|---|---|---|
| Present invention | AVICEL PH-F20 (water-insoluble insulin) | 16 | 6 | 449.35 ± 183.66 | 0.33 ± 0.10 | 0.75 ± 0.33 | 361.55 ± 167.55 |
| | AVICEL PH-F20 (water-soluble insulin) | 16 | 6 | 176.45 ± 143.46 | 0.28 ± 0.13 | 0.86 ± 0.44 | 157.33 ± 138.12 |

TABLE 1-continued

| | Kind of preparation | Dosage (IU/body) | Number of animals | $C_{max}$ (μU/mL) | $T_{max}$ (h) | $T_{1/2}$ (h) | $AUC_{0-4}$ (μU · h/mL) |
|---|---|---|---|---|---|---|---|
| | AVICEL PH-101 (water-insoluble insulin) | 16 | 6 | 164.73 ± 70.76 | 0.33 ± 0.10 | 0.78 ± 0.26 | 129.78 ± 78.45 |
| Comparison | AVICEL PH-101 (water-soluble insulin) | 16 | 6 | 153.95 ± 31.96 | 0.20 ± 0.07 | 0.96 ± 0.79 | 102.88 ± 24.16 |

Remarks:
$C_{max}$: maximum blood concentration of insulin
$T_{max}$: time to reach maximum blood concentration
$T_{1/2}$: time for maximum blood concentration to decrease by half
$AUC_{0-4}$: whole area under the blood concentration curve from 0–4 hours

TABLE 2

Administration of AVICEL PH-F20 (water-insoluble insulin) (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 60.8 | 225.2 | 239.6 | 194.6 | 149.8 | 66.9 | 10.0 | 2.3 |
| 2 | 24.1 | 349.0 | 632.0 | 529.5 | 412.5 | 181.2 | 45.4 | 15.9 |
| 3 | 18.8 | 220.3 | 708.0 | 663.0 | 471.5 | 201.4 | 35.6 | 3.5 |
| 4 | 2.9 | 124.4 | 274.5 | 307.0 | 224.0 | 61.4 | 16.6 | 5.4 |
| 5 | 76.1 | 287.0 | 413.5 | 384.5 | 214.0 | 105.5 | 20.8 | 6.4 |
| 6 | 20.4 | 396.0 | 370.0 | 211.0 | 95.9 | 24.9 | 9.2 | 4.8 |
| Average | 33.85 | 266.98 | 439.60 | 381.60 | 261.28 | 106.88 | 22.93 | 6.38 |
| Standard deviation | 28.18 | 98.01 | 190.70 | 184.77 | 148.64 | 70.49 | 14.60 | 4.88 |

TABLE 3

Administration of AVICEL PH-F20 (water-soluble insulin) (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 3.8 | 385.0 | 434.0 | 392.0 | 322.0 | 123.2 | 18.4 | 2.3 |
| 2 | 7.0 | 72.6 | 58.6 | 32.2 | 28.5 | 14.0 | 5.7 | 6.7 |
| 3 | 3.4 | 71.4 | 98.2 | 116.3 | 85.7 | 29.4 | 11.3 | 1.3 |
| 4 | 3.2 | 51.2 | 32.0 | 18.4 | 10.8 | 5.6 | 3.0 | 7.9 |
| 5 | 2.8 | 228.1 | 247.0 | 235.6 | 171.8 | 92.4 | 14.6 | 4.8 |
| 6 | 2.7 | 137.6 | 108.0 | 65.7 | 37.9 | 19.1 | 14.0 | 1.3 |
| Average | 3.82 | 157.65 | 162.97 | 143.37 | 109.45 | 47.28 | 11.17 | 4.05 |
| Standard deviation | 1.61 | 128.89 | 152.17 | 144.96 | 119.19 | 48.49 | 5.81 | 2.85 |

TABLE 4

Administration of AVICEL PH-101 (water-insoluble insulin) (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 8.2 | 80.4 | 63.9 | 32.0 | 19.4 | 8.8 | 3.4 | 3.3 |
| 2 | 5.2 | 83.0 | 162.8 | 125.6 | 96.2 | 44.7 | 9.7 | 2.7 |
| 3 | 12.7 | 159.6 | 265.0 | 265.5 | 211.4 | 103.0 | 16.8 | 5.1 |
| 4 | 2.7 | 113.1 | 182.2 | 160.3 | 73.5 | 41.0 | 4.8 | 3.2 |
| 5 | 4.5 | 62.6 | 89.8 | 40.8 | 23.8 | 13.1 | 5.1 | 3.3 |
| 6 | 5.4 | 184.7 | 207.7 | 120.2 | 56.5 | 35.7 | 5.6 | 5.5 |
| Average | 6.45 | 113.90 | 161.90 | 124.07 | 80.13 | 41.05 | 7.57 | 3.85 |
| Standard deviation | 3.54 | 48.60 | 74.76 | 85.72 | 70.65 | 33.77 | 5.00 | 1.15 |

TABLE 5

Administration of AVICEL PH-101 (water-soluble insulin) (chronological change in insulin concentration)

| Animal No. | Insulin ($\mu$U/mL) 0 | 10 min | 20 min | 30 min | 40 min | 1 hr | 2 hrs | 4 hrs |
|---|---|---|---|---|---|---|---|---|
| 1 | 0.4 | 176.6 | 172.3 | 88.0 | 58.7 | 32.6 | 10.9 | 3.6 |
| 2 | 2.0 | 127.9 | 118.3 | 73.2 | 52.3 | 21.4 | 4.2 | 1.4 |
| 3 | 1.8 | 123.2 | 160.2 | 110.3 | 109.2 | 42.7 | 6.7 | 0.6 |
| 4 | 8.6 | 153.4 | 151.6 | 76.2 | 35.9 | 16.1 | 2.0 | 2.2 |
| 5 | 6.0 | 108.8 | 71.9 | 69.0 | 35.5 | 17.3 | 5.0 | 1.9 |
| 6 | 0.9 | 196.8 | 111.5 | 73.5 | 38.5 | 17.6 | 9.4 | 7.2 |
| Average | 3.28 | 147.78 | 130.97 | 81.70 | 55.02 | 24.62 | 6.37 | 2.82 |
| Standard deviation | 3.27 | 34.01 | 37.46 | 15.42 | 28.20 | 10.74 | 3.33 | 2.37 |

Table 1 shows that when 16 IU/head of insulin was nasally administered, the most favorable insulin absorption was seen in the order water-insoluble insulin with Avicel® PH-F20, followed by water-soluble insulin with Avicel® PH-F20, water-insoluble insulin with Avicel® PH-101 (all these are the present invention), water-soluble insulin with Avicel® PH-101 (comparison), and it is clear that the compositions according to the present invention reached significantly high serum insulin concentrations in comparison with the comparative composition.

(2) Subsequent examples are of studies conducted with water-insoluble insulin, which show good absorption, using various crystalline aggregate carriers for nasal administration. 35 mg of powdered water-insoluble insulin (28.7 IU/mg), received as described above, and crystalline cellulose [Asahi Chemical Industrial Co., Ltd.: Avicel® PH-101 and Avicel® PH-301, Avicel® PH-F20, and Avicel® PH-M15 (965 mg of each)], were thoroughly mixed in a mortar to prepare nasal administration compositions, and each was administered to cynomolgus monkeys (n=6). Pharmacokinetic parameters calculated from serum insulin concentrations after administration are shown in Table 6 (mean value±SD).

Figure 3:
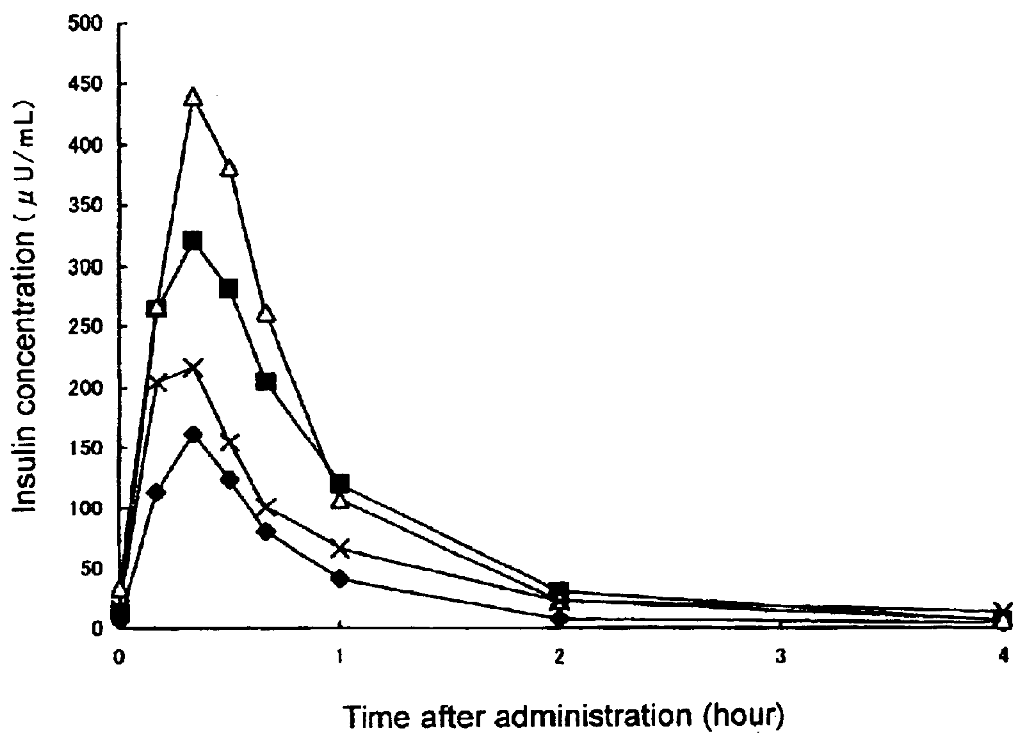
FIG. 3 is a graph showing changes in serum insulin concentrations after intranasal administration of each preparation in cynomolgus monkeys. -♦-, a preparation with Avicel® PH-101; -■-, a preparation with Avicel® PH-301; -Δ-, a preparation with Avicel® PH-F20; -*-, a preparation with Avicel® PH-M15.
Figure 4:
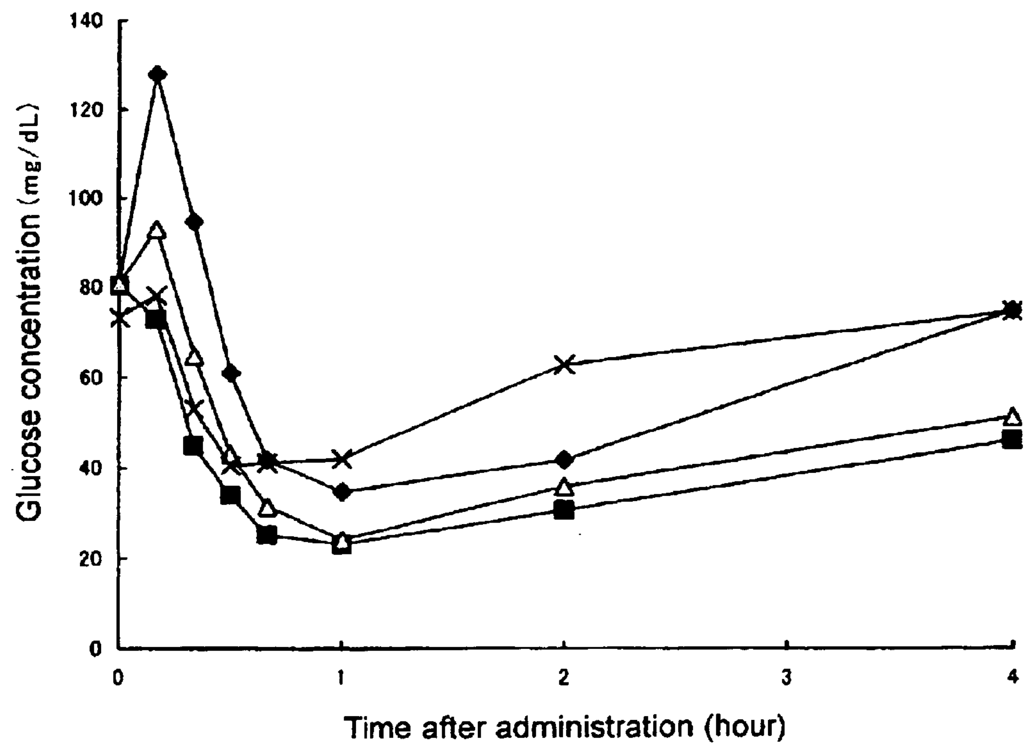
FIG. 4 is a graph showing changes in serum glucose concentrations after intranasal administration of each preparation in cynomolgus monkeys. The legends correspond to those in FIG. 3.

Serum insulin and glucose concentration-time curves after nasal administration of compositions described above are shown in FIGS. 3 and 4. Raw data relating to FIG. 3 are shown in Tables 7 to 10.

TABLE 6

| Kind of preparation | Dosage (IU/body) | Number of animals | $C_{max}$ ($\mu$U/mL) | $T_{max}$ (h) | $T_{1/2}$ (h) | $AUC_{0-4}$ ($\mu$U · h/mL) |
|---|---|---|---|---|---|---|
| AVICEL PH-101 | 16 | 6 | 164.73 ± 70.76 | 0.33 ± 0.10 | 0.78 ± 0.26 | 129.78 ± 78.45 |
| AVICEL PH-301 | 16 | 6 | 353.57 ± 174.91 | 0.39 ± 0.14 | 0.65 ± 0.10 | 328.13 ± 162.93 |
| AVICEL PH-F20 | 16 | 6 | 449.35 ± 183.66 | 0.33 ± 0.10 | 0.75 ± 0.33 | 361.55 ± 167.55 |
| AVICEL PH-M15 | 16 | 6 | 225.40 ± 89.70 | 0.28 ± 0.08 | 1.09 ± 0.53 | 214.57 ± 72.37 |

TABLE 7

Administration of AVICEL PH-101 (chronological change in insulin concentration)

| Animal No. | Insulin ($\mu$U/mL) 0 | 10 min | 20 min | 30 min | 40 min | 1 hr | 2 hrs | 4 hrs |
|---|---|---|---|---|---|---|---|---|
| 1 | 8.2 | 80.4 | 63.9 | 32.0 | 19.4 | 8.8 | 3.4 | 3.3 |
| 2 | 5.2 | 83.0 | 162.8 | 125.6 | 96.2 | 44.7 | 9.7 | 2.7 |
| 3 | 12.7 | 159.6 | 265.0 | 265.5 | 211.4 | 103.0 | 16.8 | 5.1 |
| 4 | 2.7 | 113.1 | 182.2 | 160.3 | 73.5 | 41.0 | 4.8 | 3.2 |
| 5 | 4.5 | 62.6 | 89.8 | 40.8 | 23.8 | 13.1 | 5.1 | 3.3 |
| 6 | 5.4 | 184.7 | 207.7 | 120.2 | 56.5 | 35.7 | 5.6 | 5.5 |
| Average | 6.45 | 113.90 | 161.90 | 124.07 | 80.13 | 41.05 | 7.57 | 3.85 |
| Standard deviation | 3.54 | 48.60 | 74.76 | 85.72 | 70.65 | 33.77 | 5.00 | 1.15 |

TABLE 8

| Administration of AVICEL PH-301 (chronological change in insulin concentration) | | | | | | | | |
|---|---|---|---|---|---|---|---|---|
| Animal | Insulin ($\mu$U/mL) | | | | | | | |
| No. | 0 | 10 min | 20 min | 30 min | 40 min | 1 hr | 2 hrs | 4 hrs |
| 1 | 9.1 | 129.7 | 77.0 | 41.1 | 24.2 | 19.1 | 1.8 | 1.5 |
| 2 | 20.5 | 447.5 | 586.0 | 385.0 | 241.0 | 73.8 | 18.6 | 5.3 |
| 3 | 9.4 | 185.9 | 239.0 | 367.5 | 313.5 | 225.7 | 77.6 | 4.2 |
| 4 | 22.7 | 263.0 | 387.0 | 397.5 | 293.5 | 203.3 | 40.0 | 11.6 |
| 5 | 10.9 | 419.0 | 469.5 | 326.5 | 234.8 | 119.2 | 24.9 | 7.1 |
| 6 | 7.4 | 141.2 | 167.6 | 171.2 | 122.4 | 79.2 | 19.9 | 3.8 |
| Average | 13.33 | 264.38 | 321.02 | 281.47 | 204.90 | 120.05 | 30.47 | 5.58 |
| Standard deviation | 6.54 | 139.22 | 193.09 | 143.91 | 110.72 | 80.11 | 26.14 | 3.47 |

TABLE 9

| Administration of AVICEL PH-F20 (chronological change in insulin concentration) | | | | | | | | |
|---|---|---|---|---|---|---|---|---|
| Animal | Insulin ($\mu$U/mL) | | | | | | | |
| No. | 0 | 10 min | 20 min | 30 min | 40 min | 1 hr | 2 hrs | 4 hrs |
| 1 | 60.8 | 225.2 | 239.6 | 194.6 | 149.8 | 66.9 | 10.0 | 2.3 |
| 2 | 24.1 | 349.0 | 632.0 | 529.5 | 412.5 | 181.2 | 45.4 | 15.9 |
| 3 | 18.8 | 220.3 | 708.0 | 663.0 | 471.5 | 201.4 | 35.6 | 3.5 |
| 4 | 2.9 | 124.4 | 274.5 | 307.0 | 224.0 | 61.4 | 16.6 | 5.4 |
| 5 | 76.1 | 287.0 | 413.5 | 384.5 | 214.0 | 105.5 | 20.8 | 6.4 |
| 6 | 20.4 | 396.0 | 370.0 | 211.0 | 95.9 | 24.9 | 9.2 | 4.8 |
| Average | 33.85 | 266.98 | 439.60 | 381.60 | 261.28 | 106.88 | 22.93 | 6.38 |
| Standard deviation | 28.18 | 98.01 | 190.70 | 184.77 | 148.64 | 70.49 | 14.60 | 4.88 |

TABLE 10

| Administration of AVICEL PH-M15 (chronological change in insulin concentration) | | | | | | | | |
|---|---|---|---|---|---|---|---|---|
| Animal | Insulin ($\mu$U/mL) | | | | | | | |
| No. | 0 | 10 min | 20 min | 30 min | 40 min | 1 hr | 2 hrs | 4 hrs |
| 1 | 18.0 | 264.0 | 223.9 | 125.0 | 69.2 | 37.5 | 11.8 | 6.6 |
| 2 | 10.2 | 309.5 | 348.0 | 289.0 | 202.1 | 126.5 | 26.8 | 8.9 |
| 3 | 6.6 | 158.9 | 194.4 | 179.1 | 145.5 | 102.2 | 25.4 | 7.2 |
| 4 | 23.6 | 118.5 | 140.1 | 94.5 | 60.3 | 67.6 | 40.0 | 22.8 |
| 5 | 19.1 | 288.0 | 277.0 | 136.0 | 71.9 | 38.2 | 14.2 | 17.2 |
| 6 | 24.9 | 89.5 | 117.9 | 105.6 | 55.6 | 26.3 | 17.8 | 19.0 |
| Average | 17.07 | 204.73 | 216.88 | 154.87 | 100.77 | 66.38 | 22.67 | 13.62 |
| Standard deviation | 7.29 | 94.06 | 86.09 | 71.97 | 59.63 | 40.33 | 10.38 | 6.91 |

Table 6 shows that when 16 IU/head of insulin was nasally administered, the most favorable insulin absorption was seen in the order Avicel® PH-F20, followed by Avicel® 301, Avicel® PH-M15, and Avicel® PH-101 in that order, and it is clear that the compositions according to the present invention reached significantly high serum insulin concentrations in comparison with the comparative composition. $AUC_{0-4}$ ($\mu$U·h/mL) of Avicel® PH-F20 was about three times that of Avicel® PH-101 (see FIG. 3). Avicel® PH-101 and Avicel® PH-F20 were produced serially; Avicel® PH-101 being chopped and pulverized to form Avicel® PH-F20. The method of producing Avicel® 301 and Avicel® PH-M15 was different from that of Avicel® PH-101. Avicel® PH-F20, Avicel® 301, Avicel® PH-M15, and Avicel® PH-101 have bulk densities of 0.23, 0.39, 0.53, and 0.29 g/$cm^3$, respectively.

(3) Avicel® PH-F20 derivatives were classified into particle diameters (see Table 11 for sieve distribution), of 20–25 $\mu$m (hereafter F-20 20–25 $\mu$m), 25–38 $\mu$m (hereafter F-20 25–38 $\mu$m), 38–53 $\mu$m (hereafter F-20 38–53 $\mu$m), 25–53 $\mu$m (hereafter F-20 25–53 $\mu$m), 53 $\mu$m or below (hereafter F-20 53 $\mu$m or below), and 53 $\mu$m or above (hereafter F-20 53 $\mu$m or above) and nasally administered to cynomolgus monkeys as carriers, prepared in the proportions described above, for water-insoluble insulin (16 IU/head) and serum insulin and glucose concentrations were measured. Pharmacokinetic parameters calculated from serum insulin concentrations after administration are shown in Table 12 (mean value±SD).

TABLE 11

| Sieve-through particle diameter (μm) | Sieve-through amount (g) | Sieve-through rate (%) |
|---|---|---|
| 20–25 | 1.98 | 6.6 |
| 25–38 | 12.35 | 41.2 |
| 38–53 | 13.20 | 44.0 |
| 53 or more | 2.14 | 7.1 |
| Total | 29.67 (Loss amount: 0.33 g) | 98.9 (Loss rate: 1.1%) |

TABLE 12

| Kind of preparation | Dosage (IU/body) | Number of animals | $C_{max}$ (μU/mL) | $T_{max}$ (h) | $T_{1/2}$ (h) | $AUC_{0-4}$ (μU · h/mL) |
|---|---|---|---|---|---|---|
| F20 | 16 | 6 | 449.35 ± 183.66 | 0.33 ± 0.10 | 0.75 ± 0.33 | 361.55 ± 167.55 |
| F20 20–25 μm | 16 | 6 | 191.95 ± 51.11 | 0.25 ± 0.09 | 0.74 ± 0.11 | 156.33 ± 62.74 |
| F20 25–38 μm | 16 | 6 | 291.45 ± 113.75 | 0.22 ± 0.08 | 0.91 ± 0.31 | 227.75 ± 168.21 |
| F20 38–53 μm | 16 | 6 | 364.82 ± 209.04 | 0.22 ± 0.08 | 0.62 ± 0.11 | 256.89 ± 167.69 |
| F20 25–53 μm | 16 | 6 | 232.90 ± 118.64 | 0.31 ± 0.12 | 0.93 ± 0.36 | 203.69 ± 128.28 |
| F20 53 μm or less | 16 | 6 | 280.20 ± 164.68 | 0.25 ± 0.09 | 1.23 ± 0.69 | 218.81 ± 153.03 |
| F20 53 μm or more | 16 | 6 | 194.68 ± 93.39 | 0.28 ± 0.08 | 1.01 ± 0.51 | 169.61 ± 78.58 |

Figure 5:
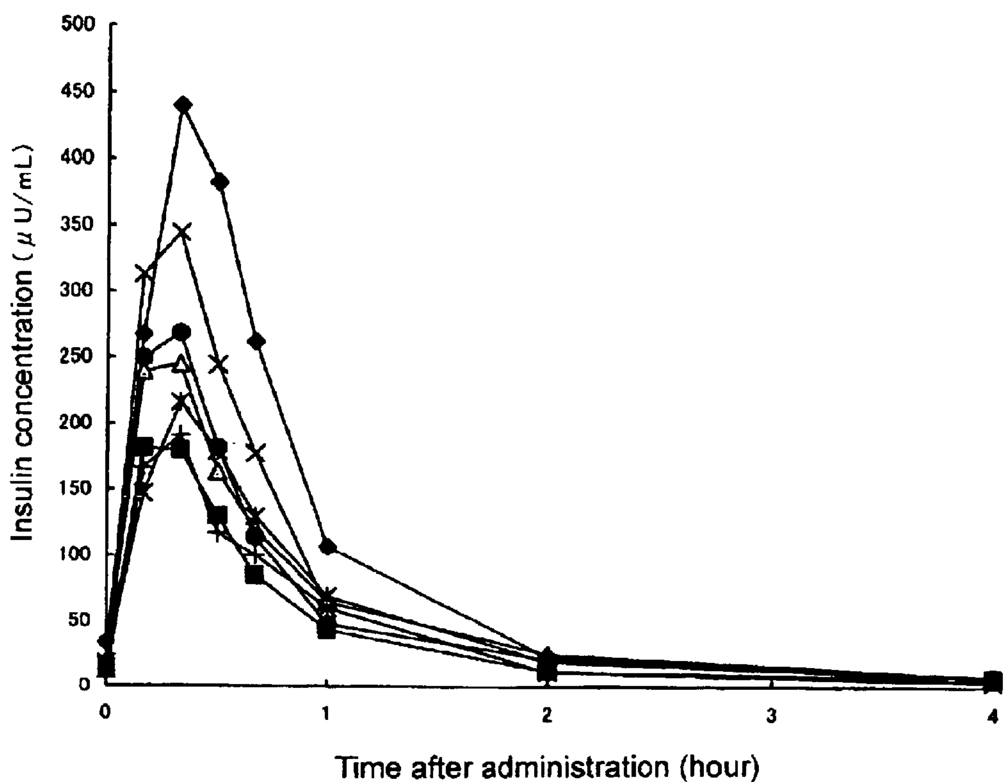
FIG. 5 is a graph showing changes in serum glucose concentrations after intranasal administration of each preparation in cynomolgus monkeys. -♦-, a preparation with Avicel® PH-F20; -■-, a preparation with Avicel® PH-F20 (20–25 μm); -Δ-, a preparation with Avicel® PH-F20 (25–38 μm); -x-, a preparation with Avicel® PH-F20 (38–53 μm); -*-, a preparation with Avicel® PH-F20 (25–53 μm); -●-, a preparation with Avicel® PH-F20 (<53 μm); -+-, a preparation with Avicel® PH-F20 (>53 μm).
Figure 6:
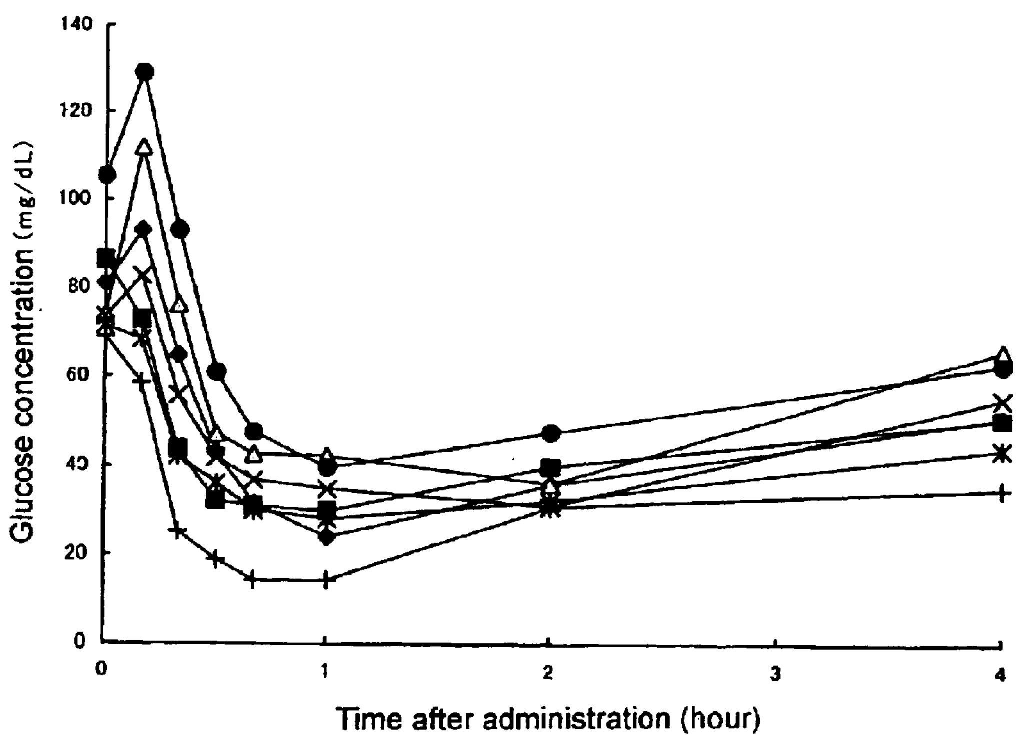
FIG. 6 is a graph showing changes in serum glucose concentrations after intranasal administration of each preparation in cynomolgus monkeys. The legends correspond to those in FIG. 5.

Serum insulin and glucose concentration-time curves after nasal administration of preparations described above are shown in FIGS. 5 and 6. Raw data relating to FIG. 5 are shown in Tables 13–19.

TABLE 13

Administration of F20 (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 60.8 | 225.2 | 239.6 | 194.6 | 149.8 | 66.9 | 10.0 | 2.3 |
| 2 | 24.1 | 349.0 | 632.0 | 529.5 | 412.5 | 181.2 | 45.4 | 15.9 |
| 3 | 18.8 | 220.3 | 708.0 | 663.0 | 471.5 | 201.4 | 35.6 | 3.5 |
| 4 | 2.9 | 124.4 | 274.5 | 307.0 | 224.0 | 61.4 | 16.6 | 5.4 |
| 5 | 76.1 | 287.0 | 413.5 | 384.5 | 214.0 | 105.5 | 20.8 | 6.4 |
| 6 | 20.4 | 396.0 | 370.0 | 211.0 | 95.9 | 24.9 | 9.2 | 4.8 |
| Average | 33.85 | 266.98 | 439.60 | 381.60 | 261.28 | 106.88 | 22.93 | 6.38 |
| Standard deviation | 28.18 | 98.01 | 190.70 | 184.77 | 148.64 | 70.49 | 14.60 | 4.88 |

TABLE 14

Administration of F20 20–25 μm (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 24.4 | 184.1 | 160.1 | 91.9 | 60.1 | 28.2 | 5.0 | 7.0 |
| 2 | 13.1 | 271.5 | 230.3 | 198.6 | 128.7 | 66.1 | 20.7 | 3.4 |
| 3 | 17.6 | 209.4 | 223.6 | 190.4 | 144.0 | 71.7 | 31.2 | 7.7 |
| 4 | 5.9 | 120.2 | 111.6 | 90.6 | 61.5 | 46.4 | 6.2 | 2.4 |
| 5 | 10.4 | 152.4 | 173.0 | 88.6 | 48.9 | 12.9 | 4.4 | 3.6 |
| 6 | 13.8 | 152.4 | 179.3 | 119.1 | 65.8 | 35.5 | 5.8 | 4.5 |
| Average | 14.20 | 181.67 | 179.65 | 129.87 | 84.83 | 43.47 | 12.22 | 4.77 |
| Standard deviation | 6.33 | 53.55 | 43.71 | 51.36 | 40.58 | 22.58 | 11.16 | 2.12 |

TABLE 15

Administration of F20 25–38 μm (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 13.4 | 217.7 | 185.0 | 102.3 | 66.3 | 59.6 | 10.7 | 9.5 |
| 2 | 44.1 | 181.5 | 334.0 | 221.9 | 145.6 | 67.4 | 16.0 | 9.0 |
| 3 | 14.0 | 341.0 | 500.0 | 449.0 | 368.0 | 196.2 | 74.9 | 6.3 |
| 4 | 13.3 | 216.9 | 125.2 | 53.6 | 39.4 | 17.6 | 9.5 | 8.1 |
| 5 | 8.3 | 200.6 | 152.6 | 79.9 | 54.1 | 21.3 | 7.4 | 6.2 |
| 6 | 2.6 | 279.5 | 171.8 | 73.9 | 47.2 | 26.3 | 32.3 | 6.4 |
| Average | 15.95 | 239.53 | 244.77 | 163.43 | 120.10 | 64.73 | 25.13 | 7.58 |
| Standard deviation | 14.47 | 59.61 | 144.77 | 152.16 | 127.42 | 67.68 | 25.99 | 1.48 |

TABLE 16

Administration of F20 38–53 μm (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 6.9 | 237.5 | 193.6 | 112.1 | 62.5 | 33.9 | 12.7 | 1.4 |
| 2 | 10.4 | 508.5 | 633.0 | 440.5 | 414.0 | 114.8 | 16.0 | 4.1 |
| 3 | 8.3 | 419.5 | 604.5 | 484.5 | 336.5 | 83.9 | 16.9 | 2.4 |
| 4 | 45.3 | 351.0 | 333.5 | 305.5 | 180.7 | 100.5 | 17.4 | 2.9 |
| 5 | 9.0 | 233.8 | 204.5 | 68.7 | 32.4 | 12.4 | 2.6 | 3.5 |
| 6 | 9.7 | 129.1 | 96.1 | 54.3 | 38.9 | 16.0 | 4.9 | 4.8 |
| Average | 14.93 | 313.23 | 344.25 | 244.27 | 177.50 | 60.25 | 11.75 | 3.18 |
| Standard deviation | 14.93 | 139.14 | 225.81 | 192.01 | 164.14 | 44.94 | 6.45 | 1.22 |

TABLE 17

Administration of F20 25–53 μm (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 39.3 | 140.5 | 80.2 | 41.7 | 23.5 | 10.0 | Hemolysis | 4.1 |
| 2 | 7.1 | 82.1 | 120.8 | 58.4 | 38.7 | 14.8 | 3.7 | 6.2 |
| 3 | 5.8 | 102.5 | 235.8 | 269.0 | 197.4 | 116.9 | 31.7 | 6.8 |
| 4 | 40.0 | 181.5 | 389.0 | 337.0 | 262.0 | 111.0 | 22.3 | 12.0 |
| 5 | 7.0 | 247.0 | 347.5 | 286.5 | 207.9 | 127.6 | 27.3 | 7.8 |
| 6 | 9.2 | 130.6 | 124.6 | 80.3 | 48.8 | 34.6 | 12.0 | 5.0 |
| Average | 18.07 | 147.37 | 216.32 | 178.82 | 129.72 | 69.15 | 19.40 | 6.98 |
| Standard deviation | 16.76 | 59.49 | 129.21 | 132.48 | 104.22 | 54.94 | 11.44 | 2.78 |

TABLE 18

Administration of F20 53 μm or less (chronological change in insulin concentration)

| Animal No. | Insulin (μU/mL) 0 | 10 min | 20 min | 30 min | 40 min | 1 hr | 2 hrs | 4 hrs |
|---|---|---|---|---|---|---|---|---|
| 1 | 30.7 | 285.5 | 242.0 | 154.7 | 88.9 | 51.0 | 7.5 | 5.4 |
| 2 | 11.3 | 348.5 | 342.0 | 220.6 | 135.0 | 34.6 | 17.8 | 8.4 |
| 3 | 3.7 | 330.0 | 464.5 | 367.5 | 287.5 | 125.0 | 81.1 | 10.7 |
| 4 | 12.3 | 76.4 | 83.6 | 50.8 | 28.0 | 14.8 | 7.5 | 14.1 |
| 5 | 18.8 | 81.6 | 56.9 | 17.5 | 18.0 | 16.6 | 6.8 | 6.8 |
| 6 | 23.9 | 373.5 | 417.5 | 278.0 | 127.3 | 45.6 | 7.2 | 5.8 |
| Average | 16.78 | 249.25 | 267.75 | 181.52 | 114.12 | 47.93 | 21.32 | 8.53 |
| Standard deviation | 9.69 | 134.99 | 170.69 | 134.26 | 97.94 | 40.59 | 29.59 | 3.35 |

TABLE 19

| Animal No. | Administration of F20 53 μm or more (chronological change in insulin concentration) Insulin (μU/mL) 0 | 10 min | 20 min | 30 min | 40 min | 1 hr | 2 hrs | 4 hrs |
|---|---|---|---|---|---|---|---|---|
| 1 | 6.6 | 84.2 | 90.5 | 61.5 | 44.5 | 17.3 | 11.2 | 6.0 |
| 2 | 4.6 | 273.5 | 334.5 | 147.5 | 99.7 | 49.4 | 8.4 | 7.9 |
| 3 | 1.6 | 130.8 | 221.1 | 195.3 | 202.3 | 176.2 | 19.3 | 7.4 |
| 4 | 13.6 | 129.8 | 133.4 | 77.2 | 78.8 | 35.5 | 11.3 | 10.1 |
| 5 | 10.5 | 260.5 | 225.0 | 147.6 | 120.1 | 55.6 | 10.6 | 4.5 |
| 6 | 3.8 | 119.1 | 131.7 | 71.8 | 26.1 | 27.4 | 8.3 | 9.2 |
| Average | 6.78 | 166.32 | 191.03 | 116.82 | 100.25 | 60.23 | 11.52 | 7.52 |
| Standard deviation | 4.49 | 79.91 | 95.11 | 54.32 | 57.14 | 58.52 | 4.04 | 2.05 |

Table 12 shows that when 16 IU/head of insulin was nasally administered, insulin absorption with unclassified F-20 particles and aggregated crystalline cellulose preparations with a particle distribution across a partial region of the diameter range was slightly lower than the maximum serum insulin concentration of F-20; however, it was significantly higher than that of the comparative composition. As a reference, the raw data of intravenous administration of insulin injection solution are shown in Table 20.

TABLE 20

| Animal No. | Intravenous administration (chronological change in insulin concentration) Insulin (μU/mL) 0 | 2 min | 5 min | 10 min | 15 min | 30 min | 1 hr | 2 hrs |
|---|---|---|---|---|---|---|---|---|
| 1 | 9.7 | 1489.0 | 671.0 | 224.6 | 76.1 | 19.0 | 5.5 | 1.3 |
| 2 | 4.8 | 1626.0 | 482.0 | 378.0 | 231.5 | 64.2 | 6.7 | 0.8 |
| 3 | 10.0 | 1330.0 | 947.0 | 454.0 | 285.5 | 86.5 | 14.2 | 1.5 |
| 4 | 22.3 | 982.5 | 391.5 | 265.0 | 150.1 | 43.2 | 6.6 | 2.1 |
| 5 | 20.4 | 1039.0 | 525.0 | 235.5 | 107.2 | 19.9 | 5.3 | 2.3 |
| Average | 13.44 | 1293.30 | 603.30 | 311.42 | 170.08 | 46.56 | 7.66 | 1.60 |
| Standard deviation | 7.54 | 279.11 | 217.04 | 100.27 | 87.01 | 29.10 | 3.71 | 0.61 |

Pharmacokinetic and Pharmacological Trials in Humans

A composition with Avicel® PH-F20 as the carrier was nasally administered once and serum insulin and glucose concentrations were measured chronologically.

Insulin and glucose concentrations were measured by Enzyme Immune Assay (EIA) and Glck•G•6•PDH, respectively.

Each pharmaceutical preparation was placed in a capsule, and administered intranasally with an administration device (Jetlizer, Unisia Jecs Corporation).

Figure 7:
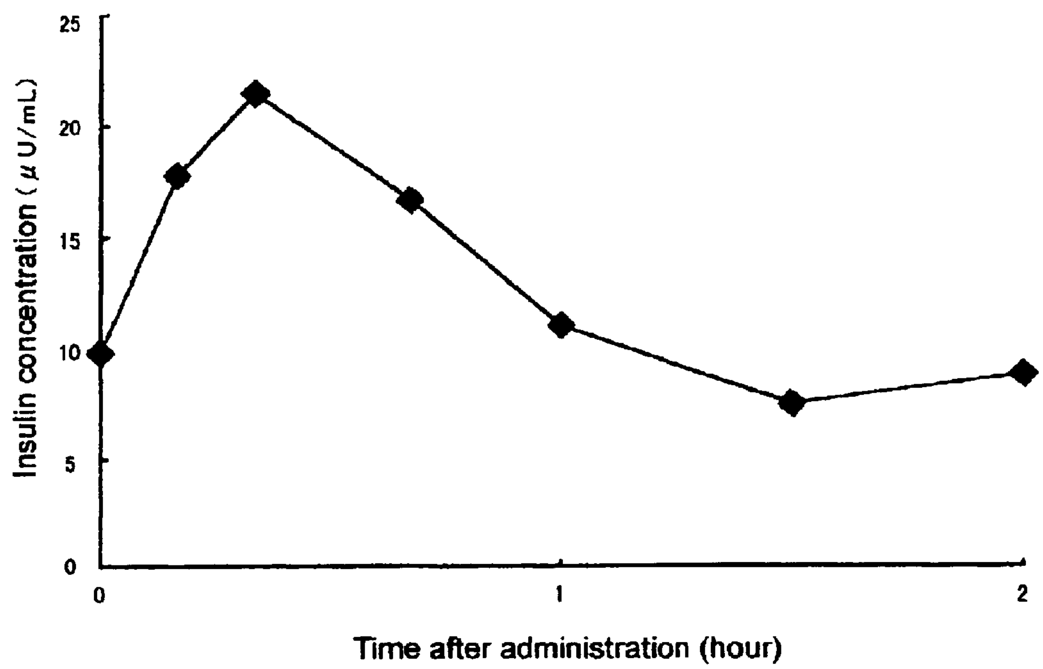
FIG. 7 is a graph showing changes in serum insulin concentrations after intranasal administration of a preparation with Avicel® PH-F20 as a carrier in humans.

35 mg of powdered water-insoluble insulin (28.7 IU/mg), was thoroughly mixed in a mortar with 965 mg of Avicel® PH-F20 (hereafter F-20) and nasally administered to three healthy adult males. Pharmacokinetic parameters calculated from serum insulin concentrations after administration are shown in Table 21 (mean value±SD). Serum insulin and glucose concentration-time curves after nasal administration of compositions described above are shown in FIGS. 7 and 8. Raw data relating to FIG. 7 are shown in Table 22.

TABLE 21

| Kind of composition | Dosage (IU/body) | Number of examinee | $C_{max}$ (μU/mL) | $T_{max}$ (h) | $T_{1/2}$ (h) | $AUC_{0-2}$ (μU · h/mL) |
|---|---|---|---|---|---|---|
| F20 | 16 | 3 | 21.80 ± 0.85 | 0.28 ± 0.09 | 1.34 ± 0.73 | 25.28 ± 5.88 |

TABLE 22

| Examinee No. | Administration of F20 (chronological change in insulin concentration) Insulin (μU/mL) 0 | 10 min | 20 min | 40 min | 1 hr | 1.5 hrs | 2 hrs |
|---|---|---|---|---|---|---|---|
| 1 | 7.9 | 17.5 | 20.9 | 14.9 | 11.8 | 10.4 | 10.4 |
| 2 | 16.6 | 21.9 | 20.8 | 19.8 | 14.0 | 8.7 | 13.8 |
| 3 | 5.1 | 13.8 | 22.6 | 15.2 | 7.4 | 3.5 | 2.5 |
| Average | 9.87 | 17.73 | 21.43 | 16.63 | 11.07 | 7.53 | 8.90 |

TABLE 22-continued

| Administration of F20 (chronological change in insulin concentration) | | | | | | | |
|---|---|---|---|---|---|---|---|
| Examinee | Insulin (μU/mL) | | | | | | |
| No. | 0 | 10 min | 20 min | 40 min | 1 hr | 1.5 hrs | 2 hrs |
| Standard deviation | 6.00 | 4.06 | 1.01 | 2.75 | 3.36 | 3.59 | 5.80 |

Figure 8:
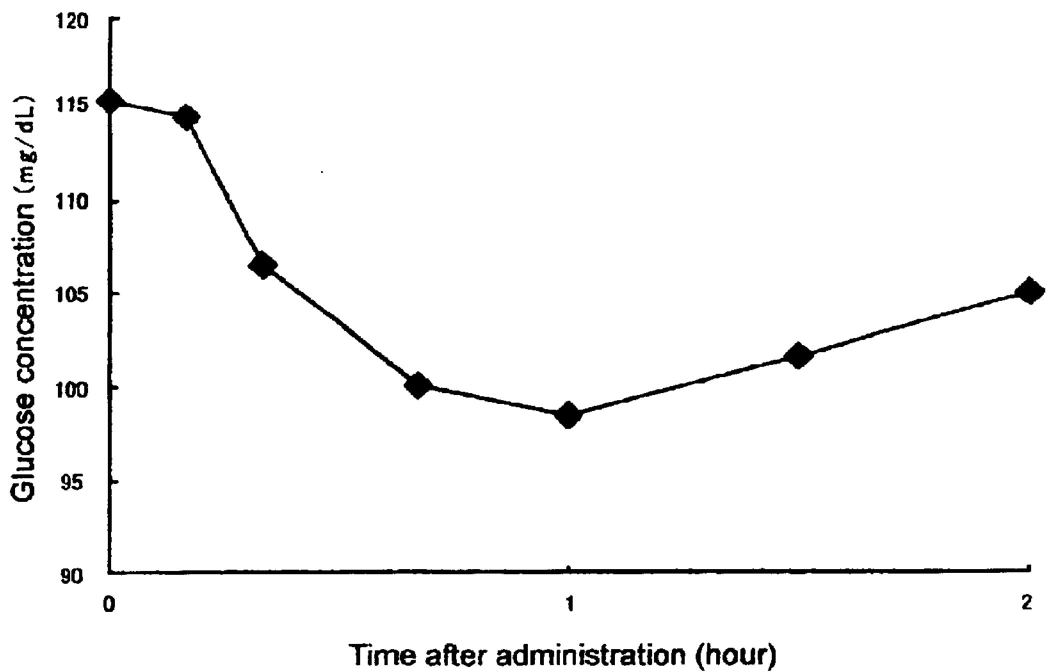
FIG. 8 is a graph showing changes in serum glucose concentrations after intranasal administration of a preparation with Avicel® PH-F20 as a carrier in humans.

Table 21 shows that granulated compositions related to the present invention show favorable serum insulin concentrations and are excellent nasal administration agents (refer to FIGS. 7 and 8).

INDUSTRIAL APPLICABILITY

Granulated compositions relating to the present invention when nasally administered to mammals, including human beings, readily and efficiently increase blood insulin concentrations. Accordingly, the present invention can be utilized by pharmaceutical producers that provide such compositions as well as by other medical industries.

What is claimed is:

1. A granulated composition for nasal administration comprising powdered insulin and its carrier, aggregated crystalline cellulose, the distinguishing features of which are that the said insulin is non-solubilized, and that 90 w/w % or more of said crystalline cellulose aggregate has a cribriform particle diameter range of 10–350 μm in one part or across the whole area, and the said granulated composition has a particle diameter falling substantially within the range of that prescribed for the said crystalline cellulose aggregate.

2. The composition as described in claim 1, in which the crystalline cellulose aggregate does not contain particles whose cribriform particle diameter substantially exceeds 150 μm.

3. The composition as described in claim 1, in which 85 w/w % or more crystalline cellulose aggregate has a cribriform particle diameter range of 20–60 μm in one part or across the whole area.

4. The composition as described in claim 1, having a cribriform particle diameter range distribution of:

w/w % or less of particle diameters below 25 μm,

20–60 w/w % of particle diameters of 25–38 μm,

20–60 w/w % of particle diameters greater than 38 μm and up to 53 μm, and 10 w/w % or less of particle diameters exceeding 53 μm, taking the entire particle as 100%.

5. The composition as described in claim 1, having a crystalline cellulose density of 0.20–0.65 g/cm$^3$.

6. A method for preparing a granulated composition for nasal administration, containing insulin, in which insulin and its carrier, aggregated crystalline cellulose, are homogeneously mixed in proportions of 1:2–100, and in which the said insulin is non-solubilized, and in which 90 w/w % or more of the said crystalline cellulose aggregate has a cribriform particle diameter range of 10–350 μm in one part or across the area.

7. The method as described in claim 6, in which 85 w/w % or more of crystalline cellulose aggregate has a cribriform particle diameter range of 20–60 μm in one part or across the whole area, and does not contain particles whose cribriform particle diameter substantially exceeds 150 μm.

8. The method as described in claim 6, wherein the composition has a cribriform particle diameter range distribution of:

10 w/w % or less of particle diameters below 25 μm,

20–60 w/w % of particle diameters of 25–38 μm,

20–60 w/w % of particle diameters greater than 38 μm and up to 53 μm, and 10 w/w % or less of particle diameters exceeding 53 μm, taking the entire particle as 100%.

9. A method of treating diabetes in which a granulated formulation comprising powdered insulin and its carrier, aggregated crystalline cellulose, the distinguishing features of which are that the said insulin is non-solubilized, and 90 w/w % or more of the said crystalline cellulose aggregate has a cribriform particle diameter range of 10–350 μm in one part or across the whole area, is sprayed into the nasal cavity of diabetes patients in a dosage that contains insulin in a sufficient amount to be an effective treatment for diabetes.

10. The therapeutic method as described in claim 9, in which 85 w/w % or more of crystalline cellulose aggregate has a cribriform particle diameter range of 20–60 μm in one part or across the whole area, and does not contain particles whose cribriform particle diameter substantially exceeds 150 μm.

11. The therapeutic method as described in claim 9, wherein the formulation has a cribriform particle diameter range distribution of:

10 w/w % or less of particle diameters below 25 μm,

20–60 w/w % of particle diameters of 25–38 μm,

20–60 w/w % of particle diameters greater than 38 μm and up to 53 μm, and 10 w/w % or less of particle diameters exceeding 53 μm, taking the entire particle as 100%.

* * * * *